United States Patent
Nonaka (10) Patent No.: US 9,501,430 B2
(45) Date of Patent: Nov. 22, 2016

(54) X-RAY IMAGING SYSTEM, INFORMATION PROCESSING APPARATUS, METHODS FOR CONTROLLING X-RAY IMAGING SYSTEM AND INFORMATION PROCESSING APPARATUS, AND RECORDING MEDIUM

(71) Applicant: CANON KABUSHIKI KAISHA, Tokyo (JP)

(72) Inventor: Hideki Nonaka, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 138 days.

(21) Appl. No.: 13/895,601

(22) Filed: May 16, 2013

(65) Prior Publication Data
US 2013/0329860 A1 Dec. 12, 2013

(30) Foreign Application Priority Data

Jun. 8, 2012 (JP) ................................. 2012-131389
Mar. 29, 2013 (JP) ................................. 2013-074865

(51) Int. Cl.
*H05G 1/56* (2006.01)
*G06F 13/14* (2006.01)
(Continued)

(52) U.S. Cl.
CPC .............. *G06F 13/14* (2013.01); *A61B 6/4494* (2013.01); *A61B 6/5294* (2013.01); *A61B 6/545* (2013.01);
(Continued)

(58) Field of Classification Search
CPC ........ A61B 6/52; A61B 6/5294; A61B 6/54; A61B 6/545; A61B 6/4294; A61B 6/548; H05G 1/56; H05G 1/58; G06F 19/34; G06F 19/3406; G06F 19/3412; G06F 19/3418; G06F 13/10; G06F 13/14; G06F 13/362; H04B 7/2662; H04B 7/2671; H04B 7/2678; H04B 7/2687; H04B 7/269; H04L 7/00; H04L 12/12; H04L 12/2424; H04L 12/2425; H04L 12/2426; H04L 41/08; H04L 41/0803; H04L 41/0806; H04L 41/0886; H04W 4/005; H04W 4/006; H04W 24/02

USPC ........... 378/91, 92, 98.8, 114–116; 700/1, 3; 710/100, 110; 712/28, 30, 31
See application file for complete search history.

(56) References Cited

U.S. PATENT DOCUMENTS 7,986,642 B2   7/2011   Ishimoto ........................ 370/255
8,174,358 B2   5/2012   Butzine et al. ................ 340/8.1
(Continued)

FOREIGN PATENT DOCUMENTS

CN        1861000        11/2006
CN      102258373        11/2011
(Continued)

OTHER PUBLICATIONS

Wi-Fi Alliance. Wi-Fi Certified for Wi-Fi Protected Setup: Easing the User Experience for Home and Small Office Wi-Fi Networks. [online]. Wi-Fi Alliance, 2007. [retrieved on Mar. 1, 2007]. Retrieved from the Internet: <URL:http://www.wifialliance.com/files/wp_18_20070108_Wi-Fi_Protected_Setup_WP_FINAL.pdf>.

(Continued)

*Primary Examiner* — Anastasia Midkiff
(74) *Attorney, Agent, or Firm* — Fitzpatrick, Cella, Harper & Scinto (57) ABSTRACT

An X-ray imaging system comprises: an x-ray sensor including a wireless slave device and a first identification information communication unit that is associated with the wireless slave device; a wireless master device configured to wirelessly connect to the wireless slave device; a second identification information communication unit that is associated with the wireless master device and an x-ray tube that irradiates x-rays; and an identification information intermediating unit configured to receive and store identification information of the wireless slave device or on the wireless master device upon approaching one of the first and the second identification information communication units, and to transmit the identification information upon approaching the other one of the first and the second identification information communication units, wherein the wireless master device and the wireless slave device establish wireless connection based on the identification information.

13 Claims, 6 Drawing Sheets

(51) Int. Cl.
*H04L 7/00* (2006.01)
*H04L 12/12* (2006.01)
*A61B 6/00* (2006.01)
*G06F 19/00* (2011.01)
*H04B 7/26* (2006.01)
*H04L 12/24* (2006.01)
*H04W 4/00* (2009.01)

(52) U.S. Cl.
CPC ........... *G06F 19/34* (2013.01); *G06F 19/3406* (2013.01); *G06F 19/3418* (2013.01); *H04B 7/269* (2013.01); *H04B 7/2662* (2013.01); *H04L 12/12* (2013.01); *H04L 41/0806* (2013.01); *H04L 41/0886* (2013.01); *H04W 4/006* (2013.01); *H05G 1/56* (2013.01); *A61B 6/4411* (2013.01); *A61B 6/548* (2013.01); *H04L 7/00* (2013.01)

(56) References Cited

U.S. PATENT DOCUMENTS

| | | | | |
|---|---|---|---|---|
| 2002/0186813 | A1* | 12/2002 | Tamura et al. | 378/98.8 |
| 2004/0176032 | A1* | 9/2004 | Kotola | G06K 7/0008 455/41.2 |
| 2006/0255904 | A1 | 11/2006 | Danzer et al. | 340/5.2 |
| 2008/0240343 | A1 | 10/2008 | Jabri et al. | 378/22 |
| 2011/0004920 | A1* | 1/2011 | Ejima | H04W 12/06 726/3 |
| 2011/0014870 | A1* | 1/2011 | Koraichi | H04W 76/025 455/41.2 |
| 2011/0108732 | A1 | 5/2011 | Watanabe | 250/370.08 |
| 2011/0110497 | A1* | 5/2011 | Nishino et al. | 378/98.8 |
| 2011/0228904 | A1* | 9/2011 | Iwakiri et al. | 378/62 |
| 2011/0274251 | A1* | 11/2011 | Omernick | G01T 7/00 378/98.8 |
| 2012/0128127 | A1* | 5/2012 | Chicchetti et al. | 378/62 |
| 2013/0064351 | A1* | 3/2013 | Urbon | A61B 6/4405 378/98.5 |
| 2013/0083897 | A1* | 4/2013 | Ohta et al. | 378/91 |
| 2013/0089183 | A1* | 4/2013 | Sura | 378/98.2 |
| 2013/0204939 | A1* | 8/2013 | Yajima | H04W 8/24 709/204 |

FOREIGN PATENT DOCUMENTS

| | | |
|---|---|---|
| EP | 1024626 A1 | 8/2000 |
| JP | 2000-224156 | 8/2000 |
| JP | 2003-172783 | 6/2003 |
| JP | 2003-338821 | 11/2003 |
| JP | 3494683 | 2/2004 |
| JP | 2008-252787 | 10/2008 |

OTHER PUBLICATIONS

Office Action issued Jan. 30, 2015, in counterpart Chinese (PRC) patent application 201310229019.9, with translation.

* cited by examiner

X-RAY IMAGING SYSTEM, INFORMATION PROCESSING APPARATUS, METHODS FOR CONTROLLING X-RAY IMAGING SYSTEM AND INFORMATION PROCESSING APPARATUS, AND RECORDING MEDIUM

BACKGROUND OF THE INVENTION

Field of the Invention

The present disclosure relates to an X-ray imaging system, an information processing apparatus, methods for controlling them, and a recording medium, and in particular relates to an X-ray imaging system for acquiring an x-ray image as digital image data by A/D conversion and transmitting the digital image data by wireless communication, an information processing apparatus, methods for controlling them, and a recording medium.

Description of the Related Art

Conventionally, digital x-ray imaging apparatuses for diagnosis have been commercialized that acquire x-ray image data from an x-ray sensor that was irradiated with x-rays, obtain digital x-ray image data by A/D conversion, and perform image processing on the digital x-ray image data. In conventional digital x-ray imaging apparatuses, in general, x-ray sensors are installed on stages or beds when used. Meanwhile, in some cases, x-ray sensors need to be freely positioned without being fixed when performing imaging, depending on imaging methods.

To meet such needs, Japanese Patent Laid-Open No. 2003-172783 discloses an apparatus in which a thin and lightweight x-ray sensor is employed so that the apparatus can be easily handled. Further, Japanese Patent No. 3494683 discloses an apparatus in which an x-ray sensor wirelessly connects to a synchronous repeater, thereby eliminating limitation of installation deriving from cables of the x-ray sensor.

To provide high-quality x-ray images, the pixel pitch in an x-ray sensor is about 100 to 200 μm, and the density resolution of 16 bits is used. Also, assuming a half-cut (43×35 cm) image area size, the data size of one image is approximately 7.5 to 30 MBytes. To perform imaging at free positions and display an x-ray image on a display or the like at a speed of several seconds after acquisition of x-ray image data of this size, a wireless communication unit is also required to achieve adequate high-speed performance. Therefore, to readily achieve high-speed performance, wireless communication using a radio wave method is employed.

If, for example, wireless LAN technology is employed as a communication method, it is necessary, in order to establish wireless connection between devices, to configure identical settings of an SSID (Service Set Identifier), an authentication method, an encryption type, an encryption key, and the like among the devices to be connected. Usually, these settings are set manually in both devices to be wirelessly connected, or are set by a push-button method defined in WPS (Wi-Fi Protected Setup) or by a PIN code method that is also defined in WPS, or the like.

Also, Japanese Patent Laid-Open No. 2000-224156 discloses, as a method for conveniently configuring these settings, a method in which a user configures settings by connecting a device that the user carries to another device to which the user wants to establish wireless connection, or by bringing these two devices close to each other, or by pointing the direction of the device to which the user wants to establish wireless connection.

Meanwhile, in the case of configuring settings manually, input operations are always needed, and the possibility that connection cannot be established due to an operation error cannot be eliminated. In the PIN code method of WPS, a PIN code needs to be input usually by using a keyboard or the like on a master device side for a slave device that outputs the PIN code. Also, in the push-button method of WPS and in the method disclosed in Japanese Patent Laid-Open No. 2000-224156, special operations that are not required in usual workflows of an x-ray imaging apparatus are necessary, such as simultaneously pressing or touching buttons of both a slave device and a master device, or bringing these devices close to each other.

SUMMARY OF THE INVENTION

According to some embodiments of the present invention, there is provided an X-ray imaging system comprising: an x-ray sensor including a wireless slave device and a first identification information communication unit that is associated with the wireless slave device; a wireless master device configured to wirelessly connect to the wireless slave device; a second identification information communication unit that is associated with the wireless master device and an x-ray tube that irradiates x-rays; and an identification information intermediating unit configured to receive and store identification information of the wireless slave device or on the wireless master device upon approaching one of the first and the second identification information communication units, and to transmit the identification information upon approaching the other one of the first and the second identification information communication units, wherein the wireless master device and the wireless slave device establish wireless connection based on the identification information.

According to some embodiments of the present invention, there is provided an X-ray imaging system comprising: an x-ray imaging device including a first identification information communication unit; and a mobile terminal including a communication unit configured to communicate with the first identification information communication unit and a second identification information communication unit associated with an x-ray generating unit, and a selecting unit configured to select a set including the x-ray imaging device and the x-ray generating unit in accordance with communication by the communication unit.

According to some embodiments of the present invention, there is provided an X-ray imaging system comprising: an x-ray sensor including a wireless communication unit and a first identification information communication unit that is associated with the wireless communication unit, a second identification information communication unit that is associated with a wireless master device wirelessly connected to the wireless slave device and with an x-ray tube configured to irradiate x-rays, and an identification information intermediating unit configured to receive and store identification information of the wireless slave device or on the wireless master device upon approaching the wireless master device and one of the first and the second identification information communication units, and to transmit the identification information upon approaching the other one of the first and the second identification information communication units, wherein the wireless slave device establishes wireless connection based on the identification information.

According to some embodiment of the present invention, there is provided an information processing apparatus comprising: an identification information intermediating unit configured to receive and store identification information of a wireless slave device included in an x-ray sensor or on a wireless master device upon approaching one of a first identification information communication unit that is associated with the wireless slave device and a second identification information communication unit that is associated with the wireless master device and with an x-ray tube that irradiates x-rays, and configured to transmit the identification information upon approaching the other one of the first and the second identification information communication units.

According to some embodiment of the present invention, there is provided a method for controlling an X-ray imaging system including an x-ray sensor having a wireless slave device and a first identification information communication unit that is associated with the wireless slave device, a wireless master device configured to wirelessly connect to the wireless slave device, a second identification information communication unit that is associated with the wireless master device and with an x-ray tube that irradiates x-rays, and an identification information intermediating unit, the method comprising: an identification information intermediating step in which the identification information intermediating unit receives and stores identification information of the wireless slave device or on the wireless master device upon approaching one of the first and the second identification information communication units, and transmits the identification information upon approaching the other one of the first and the second identification information communication units, and an establishing step in which the wireless master device and the wireless slave device establish wireless connection based on the identification information.

According to some embodiment of the present invention, there is provided a method for controlling an information processing apparatus including an identification information intermediating unit, the method comprising: an identification information intermediating step in which the identification information intermediating unit receives and stores identification information of a wireless slave device or of a wireless master device upon approaching one of a first identification information communication unit that is associated with the wireless slave device included in an x-ray sensor and a second identification information communication unit that is associated with the wireless master device and with an x-ray tube that irradiates x-rays, and transmits the identification information upon approaching the other one of the first and the second identification information communication units.

Further features of the embodiment of the present invention will become apparent from the following description of exemplary embodiments (with reference to the attached drawings).

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
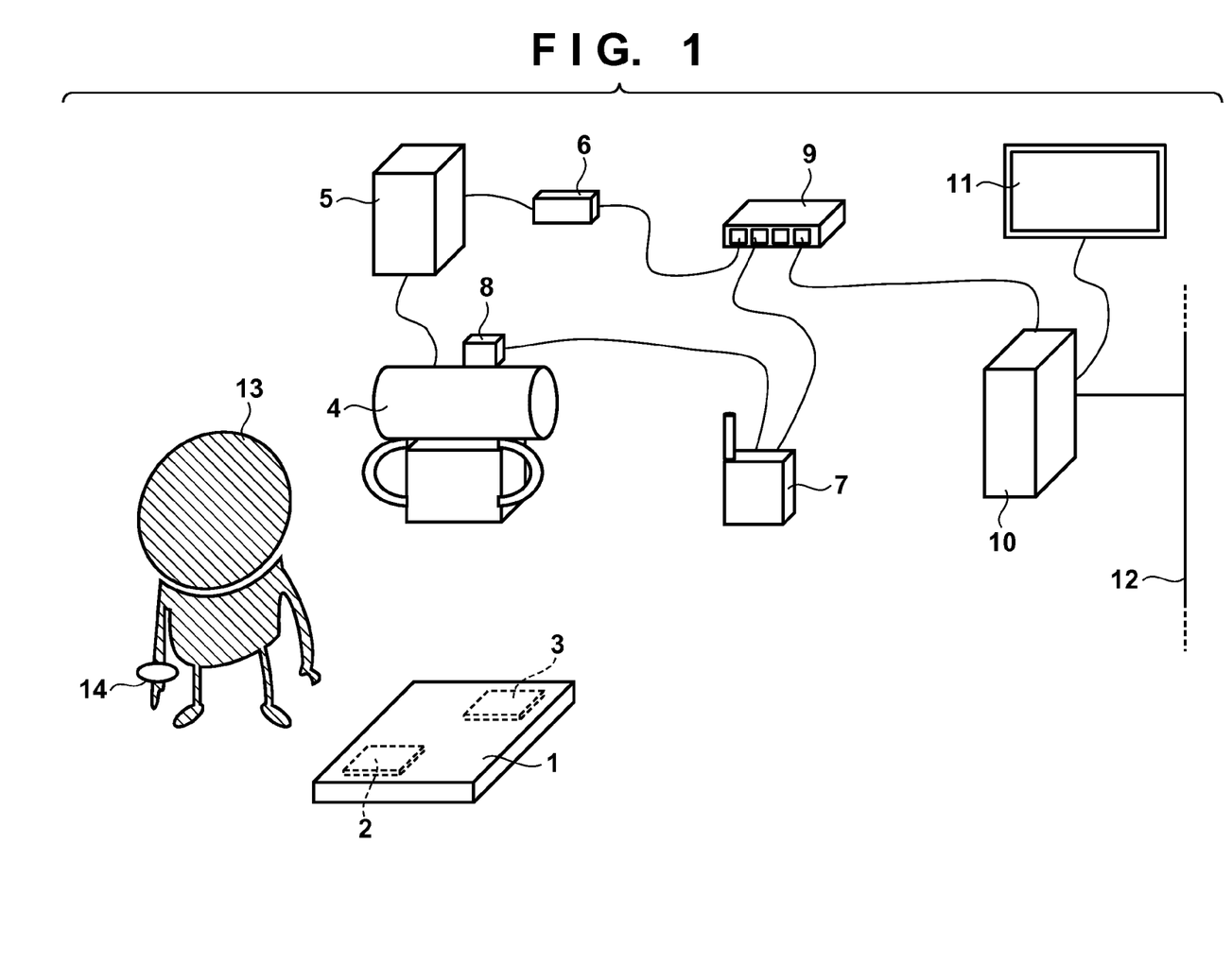
FIG. 1 is a diagram showing an exemplary overall configuration of an X-ray imaging system according to an embodiment of the present invention.

FIG. 1 is a diagram showing an exemplary overall configuration of an X-ray imaging system 100 according to the present embodiment. The X-ray imaging system 100 according to the present embodiment includes an X-ray sensor 1, an X-ray tube 4, a wireless master device 7, an identification information communication unit 8 (referred to herein as a "second" identification information communication unit because that is what it is termed in some of the claims), and an identification information intermediating unit 14 that functions as an information processing apparatus that an operator 13 wears or carries.

In FIG. 1, the x-ray sensor 1, which contains a first identification information communication unit 2 and a wireless slave device 3, detects an x-ray irradiated by the x-ray tube 4 under the control of an x-ray control device 5 and generates digital image data. An x-ray interface device 6 connects the x-ray control device 5 to a switching hub 9.

The wireless slave device 3 wirelessly communicates with the wireless master device 7 according to IEEE802.11 or the like. The wireless master device 7 opposes the wireless slave device 3 and performs wireless communication by a radio wave method, and also performs communication with an x-ray interface device 6 and an image processing apparatus 10 using Ethernet (registered trademark). The switching hub 9 connects the devices that are connected thereto using Ethernet to one another with a star topology. An image processing apparatus 10 is a personal computer (PC) or the like, and performs image processing on the generated digital image data. A display device 11 displays an image-processed digital x-ray image and an operation screen. A trunk network 12 is a network within a hospital or the like that is connected to the image processing apparatus 10.

For the x-ray sensor 1 to capture an x-ray image, it is necessary to irradiate x-rays from the x-ray tube 4 synchronously with the operation of the x-ray sensor 1. For this purpose, an x-ray synchronization signal is exchanged by communication between the x-ray sensor 1 and the x-ray control device 5. Also, for the x-ray sensor 1 to display a captured x-ray image on the display device 11, communication with the image processing apparatus 10 is necessary. All these kinds of communication are performed by wireless communication between the wireless slave device 3 and the wireless master device 7.

To establish wireless communication between the wireless slave device 3 and the wireless master device 7, it is necessary to set an SSID that serves as an identifier for the wireless network, an encryption key for encryption of communication, and the like in both the wireless slave device 3 and the wireless master device 7.

Figure 2:
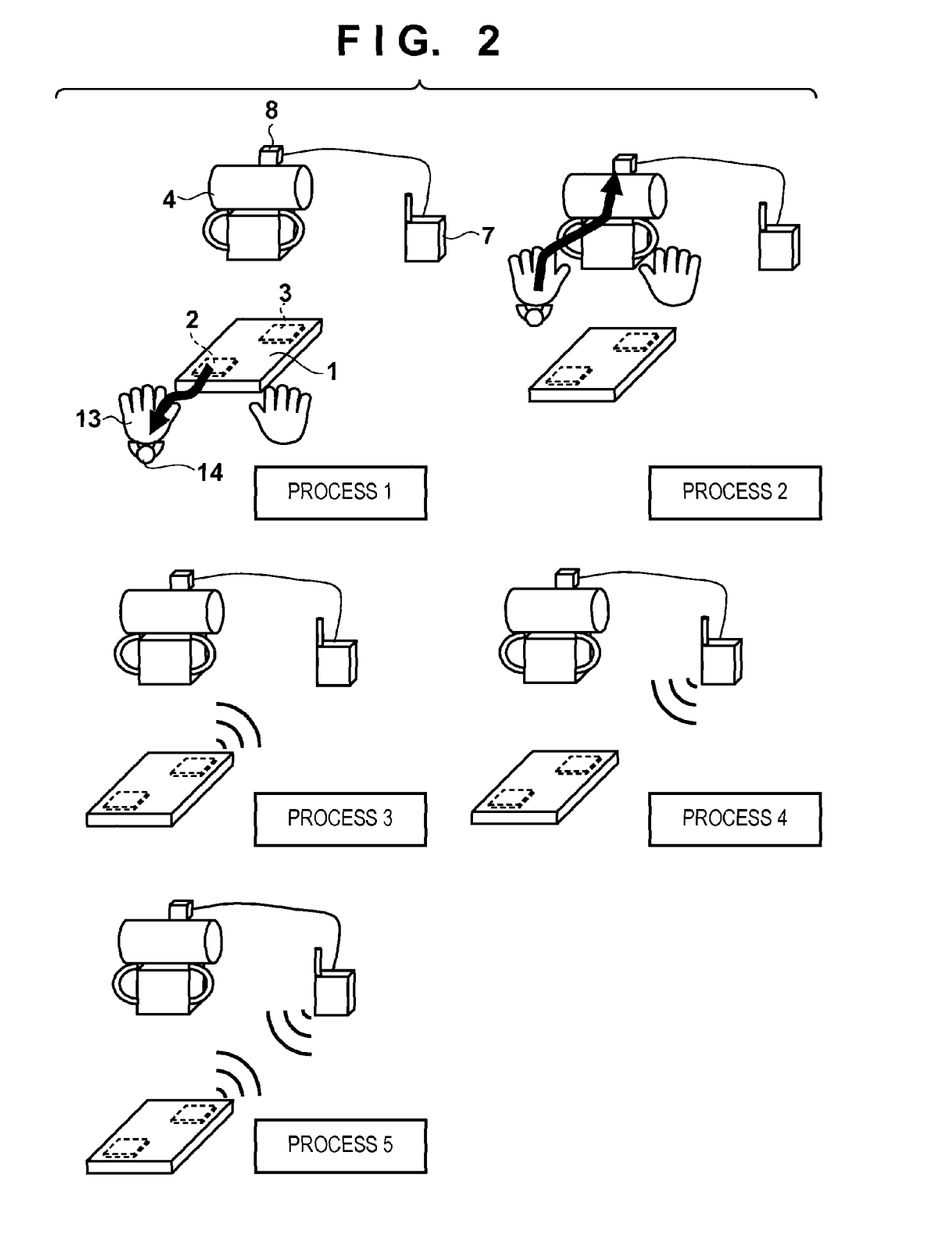
FIG. 2 is a diagram illustrating processes executed by an X-ray imaging system according to a first embodiment.
Figure 3:
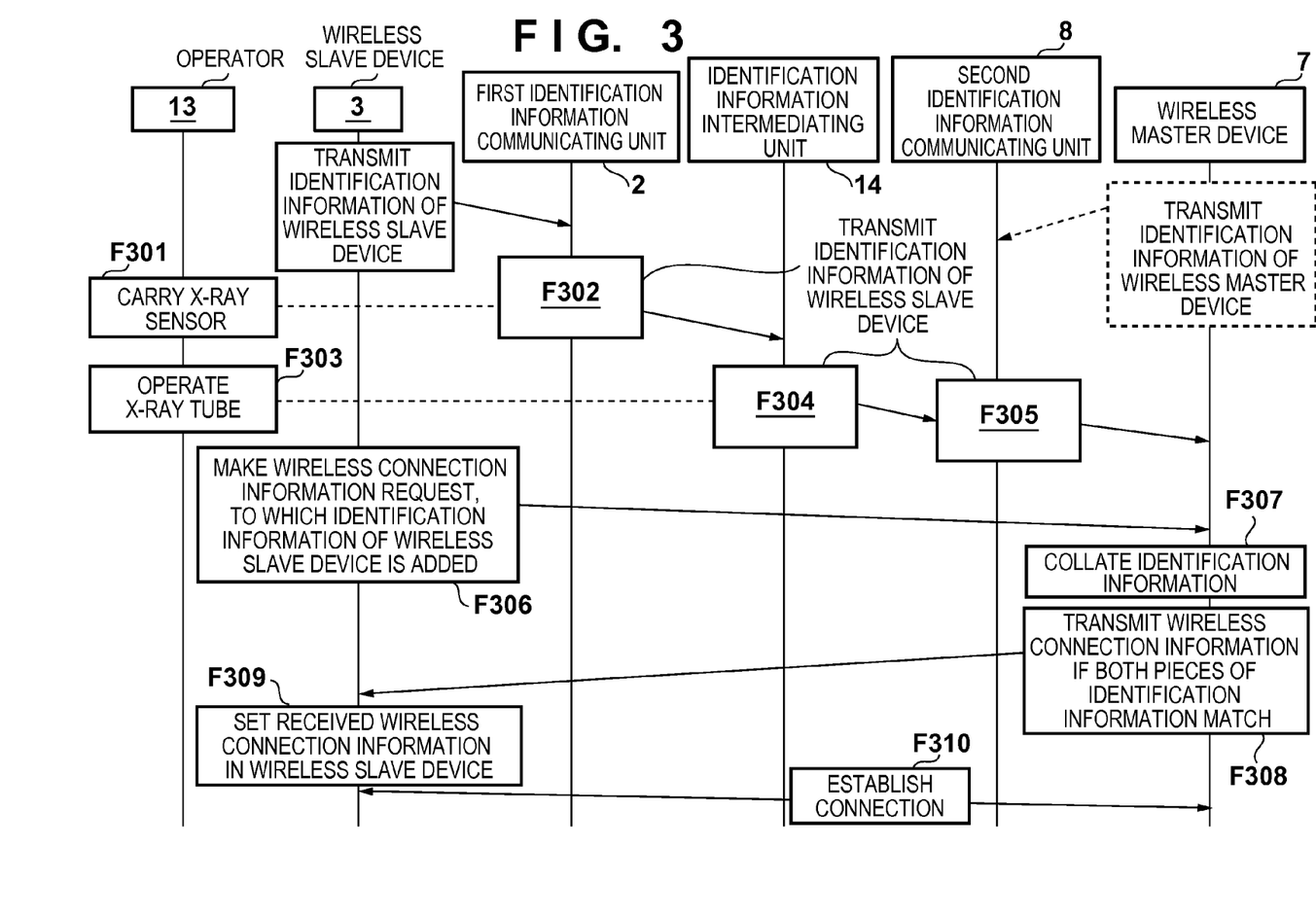
FIG. 3 is a sequence diagram showing processing executed by the X-ray imaging system according to the first embodiment.

Exemplary processes of establishment of wireless communication in the present embodiment are shown in FIG. 2, and a specific processing procedure is shown in FIG. 3. Here, as a general workflow of the operator at the time of x-ray imaging, an operation is assumed of disposing the x-ray sensor 1 with respect to a patient, and subsequently disposing the x-ray tube 4 to align with an image-receiving face of the x-ray sensor 1.

Prior to the operation by the operator 13, identification information of the wireless slave device 3 is transmitted from the wireless slave device 3 to the first identification information communication unit 2. Here, the identification information is a code indicating the class of the device (wireless slave device) to which a password that is unique to the wireless slave device 3 is added. The first identification information communication unit 2 holds the identification information received from the wireless slave device 3.

Although identification information of the wireless master device 7 may be similarly transmitted from the wireless master device 7 to the second identification information communication unit 8, this is not essential because it is assumed here that the operator 13 operates the x-ray sensor 1 first and then operates the x-ray tube 4. In practice, it is unknown whether the operator 13 operates the x-ray sensor 1 or the x-ray tube 4 first. In other words, the order of operation cannot be decided in advance, and it is therefore more preferable to implement the embodiment of the present invention based on an assumption that the operation is possibly performed in a reverse order.

Upon the operator 13 holding the x-ray sensor 1 to dispose it at an imaging region of a patient as shown in "process 1" in FIG. 2 (F301 in FIG. 3), the identification information of the wireless slave device 3 is transmitted from the first identification information communication unit 2 within the x-ray sensor 1 to the identification information intermediating unit 14 carried by the operator 13 (F302). Communication between the first identification information communication unit 2 and the identification information intermediating unit 14 is performed by the operator 13 holding the x-ray sensor 1, and no other operations are required. Therefore, as communication media, those for near field wireless communication with which communication is possible only at a very limited distance are available, such as a contactless IC card, TransferJet (trademark), BlueTooth (registered trademark), ZigBee (registered trademark), and infrared data communication.

Also, body area network communication technology has been developed and commercialized in recent years in which weak modulated current is applied to a human body, thereby using the human body as a communication path. In the present embodiment, body area network communication is preferable communication technology because, in this case, the operator 13 touching the x-ray sensor 1 or the x-ray tube 4 is used as a trigger for transmitting the identification information.

In the present embodiment, it is necessary to exchange the identification information when the operator 13 approaches, or comes in contact with, the x-ray sensor 1 or the x-ray tube 4. Therefore, the identification information intermediating unit 14 is carried by the operator 13. For the sake of workability of the operator 13, and in order that the identification information intermediating unit 14 reliably comes within an area in which near field wireless communication is possible, the identification information intermediating unit 14 in the form of a wrist band is assumed in the present embodiment.

Next, upon the operator 13 disposing the x-ray tube 4 to align with the image-receiving face of the x-ray sensor 1 as shown in "process 2" in FIG. 2 (F303), the identification information is transmitted from the identification information intermediating unit 14 carried by the operator 13 to the second identification information communication unit 8 disposed in the vicinity of the x-ray tube 4 (F304). Here again, communication between the identification information intermediating unit 14 and the second identification information communication 8 unit is performed by the operator 13 approaching, or coming in contact with, the x-ray tube 4, and no other operations are required. The second identification information communication unit 8 transfers the received identification information to the wireless master device 7 (F305).

Then, as shown in "process 3" in FIG. 2, the wireless slave device 3 within the x-ray sensor 1 makes a wireless connection information request, to which the same identification information as the information that was transmitted to the identification information intermediating unit 14 is added (S306, connection request transmission process). At this point, the wireless slave device 3 cannot recognize the presence of the wireless master device 7, and therefore, the request is broadcast. Also, although this process is performed after the identification information communication via the identification information intermediating unit 14 (F302), in practice, it may alternatively be performed immediately after the wireless slave device is activated.

Further, as shown in "process 4" in FIG. 2, the wireless master device 7 that received the wireless connection information request verifies if the identification information added to the request matches the identification information that was received and acquired from the second identification information communication unit 8 (F307). If these pieces of identification information match, the wireless master device 7 transmits the wireless connection information to the wireless slave device 3 that transmitted the request (F308, connection information transmission process). The wireless connection information to be transmitted here is information of an SSID, an authentication method, an encryption type, an encryption key, and the like, which are needed to be set identically between the wireless master device 7 and the wireless slave device 3. On the other hand, if these pieces of identification information do not match as a result of verification, the wireless connection information is not transmitted. Upon receiving the wireless connection information from the wireless master device 7, the wireless slave device 3 sets the received wireless connection information therein (F309).

As a result, wireless communication is established between the wireless slave device 3 and the wireless master device 7 as shown in "process 5" in FIG. 2, and thereafter, exchange of the x-ray synchronization signal between the x-ray sensor 1 and the x-ray control device 5 and transmission and receipt of an operation control signal and image data between the x-ray sensor 1 and the image processing apparatus 10 are possible, and these devices function as an X-ray imaging system. (F310).

As described above, according to the present embodiment, the operator can establish wireless communication only by performing the work flow for usual x-ray imaging, without performing any special operation for establishing wireless communication.

Second Embodiment

In the first embodiment, the case was described where the x-ray sensor 1 is operated first, and subsequently the x-ray tube 4 is operated. On the contrary, in the present embodiment, a case will be described where the operator 13 operates the x-ray tube 4 first, and sequentially operates the x-ray sensor 1, which is the reverse order of the operator's work flow in the first embodiment. Note that the configuration of the X-ray imaging system is the same as that of the first embodiment, and a description thereof will be omitted.

Figure 4:
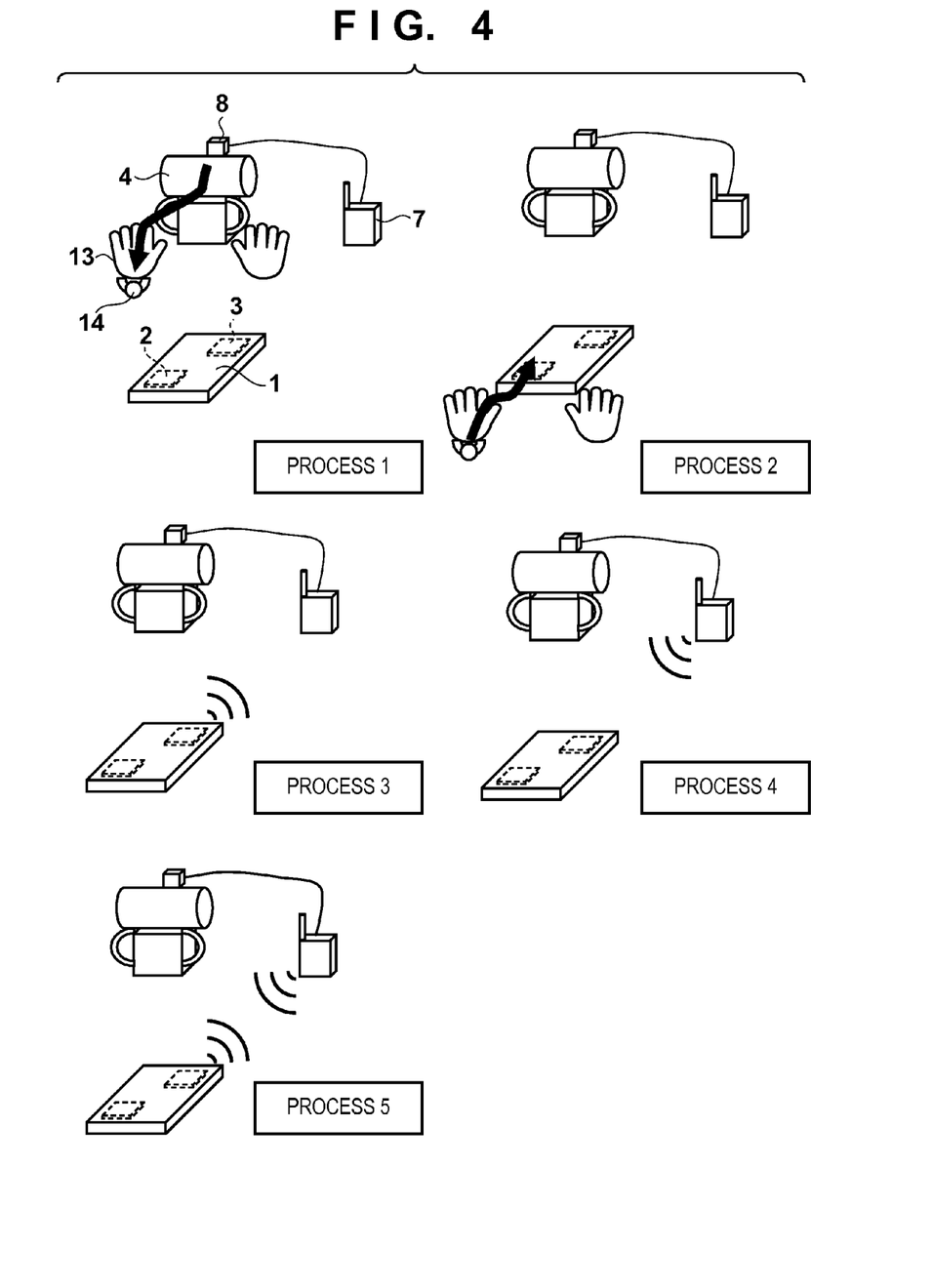
FIG. 4 is a diagram illustrating processes executed by an X-ray imaging system according to a second embodiment.
Figure 5:
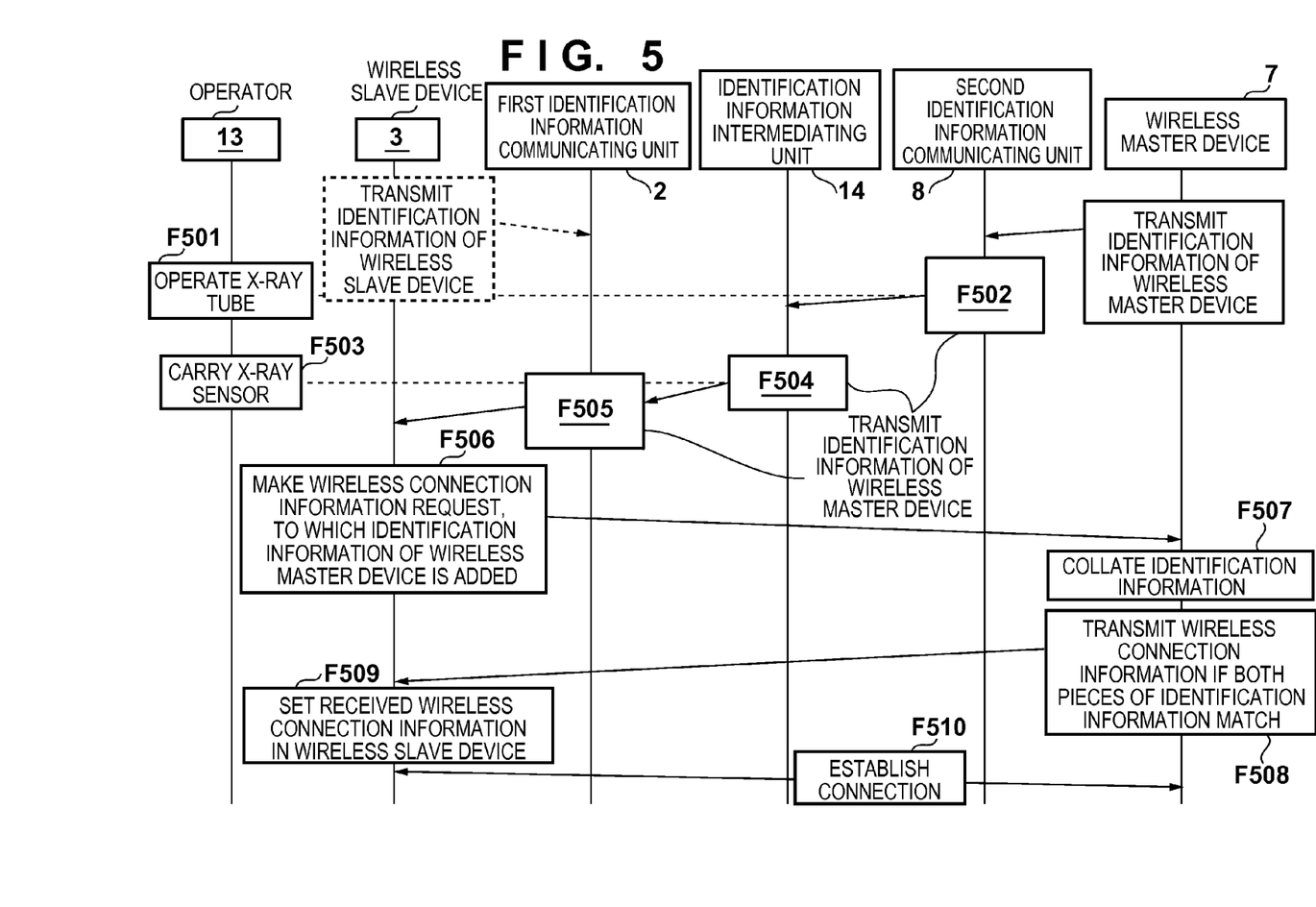
FIG. 5 is a sequence diagram showing processing executed by the X-ray imaging system according to the second embodiment.

Exemplary processes of establishment of wireless communication in the present embodiment described below are shown in FIG. 4, and a specific processing procedure is shown in FIG. 5.

Prior to the operation by the operator 13, identification information of the wireless master device 7 is transmitted from the wireless master device 7 to the second identification information communication unit 8. Here, the identification information is a code indicating the class of the device (wireless master device) to which a password that is unique to the wireless master device 7 is added. The second identification information communication unit 8 holds the identification information received from the wireless master device 7.

Although identification information of the wireless slave device 3 may be similarly transmitted from the wireless slave device 3 to the first identification information communication unit 2, this is not essential because it is assumed here that the operator 13 operates the x-ray tube 4 first, and then operates the x-ray sensor 1. In practice, it is unknown whether the operator 13 operates the x-ray sensor 1 or the x-ray tube 4 first. In other words, the order of operation cannot be decided in advance, and it is therefore more preferable to implement the embodiment of the present invention based on an assumption that the operation is possibly performed in a reverse order.

Upon the operator 13 operating the x-ray tube 4 as shown in "process 1" in FIG. 4 (F501 in FIG. 5), the identification information is transmitted from the second identification information communication unit 8 disposed in the vicinity of the x-ray tube 4 to the identification information intermediating unit 14 carried by the operator 13 (F502). Communication between the second identification information communication unit 8 and the identification information intermediating unit 14 is performed by the operator 13 operating the x-ray tube 4, and no other operations are required.

Next, as shown in "process 2" in FIG. 4, upon the operator 13 holding the x-ray sensor 1 (F503), the identification information is transmitted from the identification information intermediating unit 14 carried by the operator 13 to the first identification information communication unit 2 within the x-ray sensor 1 (F504). Here also, communication between the identification information intermediating unit 14 and the first identification information communication unit 2 is performed by the operator 13 holding the x-ray sensor 1, and no other operations are required. The first identification information communication unit 2 transfers the received identification information to the wireless slave device 3 (F505).

In subsequent "process 3" to "process 5" in FIG. 4, the same procedure is performed as in the case where the operator 13 operates the x-ray sensor 1 first and then operates the x-ray tube 4, except that the identification information in the present embodiment is the identification information of the wireless master device 7 (F506 to F510). Here, the wireless master device 7 verifies if its own identification information matches the identification information of the wireless master device 7 that was received and acquired from the wireless slave device in accordance with the wireless connection request transmission process of F506 (F507).

As described above, according to the present embodiment, the operator can establish wireless communication only by performing the work flow for usual x-ray imaging, without performing any special operation for establishing wireless communication.

Third Embodiment

In a third embodiment, a case is assumed that, in each of the first and second embodiments, there are a plurality of sets including the x-ray tube 4 as well as the second identification information communication unit 8 and the wireless master device 7 that are disposed in the vicinity of the x-ray tube 4. For the sake of simplification, it is assumed here that a set including an x-ray tube 4, a second identification information communication unit 8, and a wireless master device 7 and a set including an x-ray tube 4', a second identification information communication unit 8', and a wireless master device 7' exist. It is also assumed that wireless communication with the wireless master device 7 is currently established as a result of the operator 13 operating the x-ray sensor 1 first and then operating the x-ray tube 4 as in the first embodiment. At this time, the identification information intermediating unit 14 carried by the operator 13 stores the identification information of the wireless slave device 3 that was received in "process 1" in FIG. 2. If the operator 13 operates the other x-ray tube 4' in this state, "process 2" and subsequent processes in FIG. 2 can be performed to establish connection of the x-ray tube 4' to the second identification information communication unit 8' and the wireless master device 7'. In other words, the information that is currently stored in the identification information intermediating unit 14 does not need to be updated. On the other hand, it is now assumed that wireless communication with the wireless master device 7 is currently established as a result of the operator 13 operating the x-ray tube 4 first and then operating the x-ray sensor 1 as in the second embodiment. At this time, the identification information intermediating unit 14 carried by the operator 13 stores the identification information of the wireless master device 7 that was received in "process 1" in FIG. 4. If the operator 13 operates the other x-ray tube 4' in this state, the processes from "process 1" in FIG. 4 need to be performed to establish connection among the x-ray tube 4', the second identification information communication unit 8', and the wireless master device 7'. In other words, update of the information in the identification information intermediating unit 14 is necessary.

Further, a case is assumed here where a plurality of x-ray sensors 1 exist. For the sake of simplification, it is assumed that two x-ray sensors exist, which are an x-ray sensor 1 and an x-ray sensor 1'.

It is assumed that wireless communication with the wireless master device 7 is currently established as a result of the operator 13 operating the x-ray sensor 1 first and then operating the x-ray tube 4 as in the first embodiment. At this time, the identification information intermediating unit 14 carried by the operator 13 stores the identification information of the wireless slave device 3 that was received in "process 1" in FIG. 2. If the operator 13 holds the other x-ray sensor 1' in this state, the processes from "process 1" in FIG. 2 can be performed to connect the wireless slave device 3' to the wireless master device 7. In other words, update of the information in the identification information intermediating unit 14 is necessary.

On the other hand, it is assumed that wireless connection to the wireless master device 7 is currently established as a result of the operator 13 operating the x-ray tube 4 first and then operating the x-ray sensor 1 as in the second embodiment. At this time, the identification information intermediating unit 14 carried by the operator 13 stores the identification information of the wireless master device 7 that was received in "process 1" in FIG. 4. If the operator 13 holds the other x-ray sensor 1' in this state, the processes from "process 2" in FIG. 4 can be performed to connect the wireless slave device 3' to the wireless master device 7. In other words, the information that is currently stored in the identification information intermediating unit 14 does not need to be updated.

As described above, if the information that is currently stored in the identification information intermediating unit 14 is the identification information of the wireless master device 7, the identification information needs to be updated only in a case where the other x-ray tube 4' (which is associated with the wireless master device 7') is operated next. Similarly, if the information stored in the identification information intermediating unit 14 is the identification information of the wireless slave device 3, the identification information needs to be updated only in a case where the other x-ray sensor 1' (which is associated with the wireless slave device 3') is operated next.

In other words, the identification information stored in the identification information intermediating unit 14 is updated only in the case where the device class code is identical to that in the identification information that is currently stored in the identification information intermediating unit 14 and a password unique to each device is different, and it is thereby possible to establish wireless communication without any problem even in an X-ray imaging system having a plurality of wireless master devices (x-ray tubes) and a plurality of wireless slave devices (x-ray sensors).

Fourth Embodiment

Figure 6:
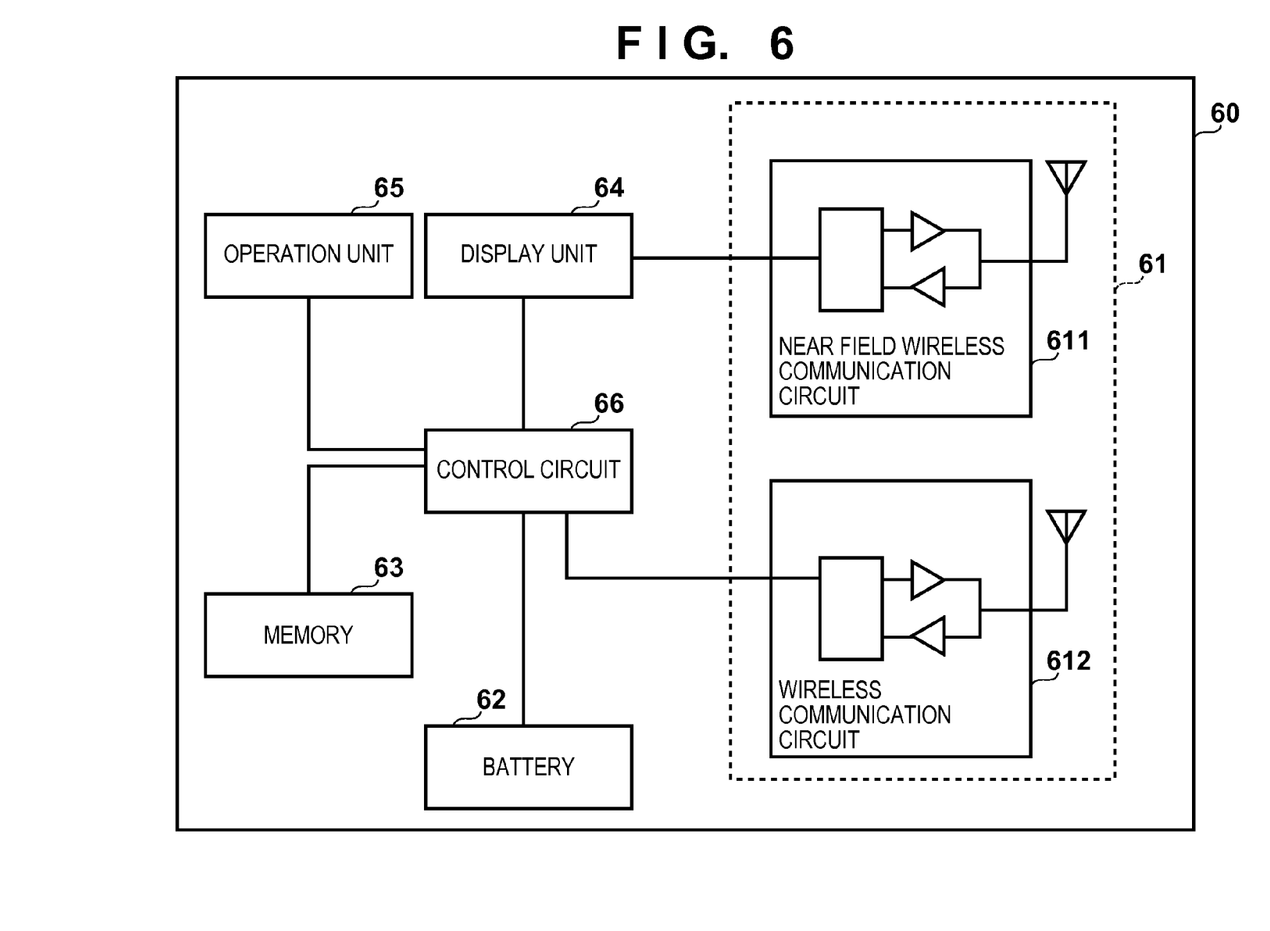
FIG. 6 is a diagram showing an exemplary overall configuration of a mobile terminal according to a fourth embodiment.

A fourth embodiment of the identification information intermediating unit 14 will be described with reference to FIG. 6. Although the mobile terminal (identification information intermediating unit) 14 used in the above-described embodiment is a terminal in the form of a wrist band, it is not limited thereto, and a mobile terminal 60 may be used that includes a communication circuit 61, a battery 62, a memory 63, a display unit 64, an operation unit 65 of a touch-panel type or the like, and a control circuit 66 for comprehensively controlling these components. The control circuit 66 receives inputs, which are information on the battery 62 and information acquired from the memory 63, the communication circuit 61, and the operation unit 65, performs calculation using the information, and executes output to the communication circuit 61, the battery 62, the memory 63, the display unit 64, and the operation unit 65, and various kinds of control. The control circuit 66 includes, for example, a CPU, a work memory, and a memory that stores a program for realizing functions for the CPU that will be described later, and is achieved by the CPU executing instructions included in the program sequentially or in parallel to execute input, calculation, output, and control. Alternatively, it is achieved by describing the aforementioned program in a hardware description language, and implementing the program as configuration data using an FPGA. The communication circuit 61 includes a near field wireless communication circuit 611 capable of near field wireless communication such as NFC (Near Field Communication) or infrared communication, and is used in an X-ray imaging system including the x-ray sensor 1 and the x-ray control device 5 that also have an NFC communication circuit. At the time of use, this mobile terminal is brought close to the x-ray sensor 1 and the x-ray control device 5, and thus the mobile terminal 60 can intermediate between the identification information of the x-ray sensor 1 and the identification information of the x-ray control device 5. This processing is the same as that in the above-described embodiments. It is thereby possible to associate the x-ray sensor 1 with the x-ray control device 5 using the aforementioned mobile terminal.

In addition, for example, the mobile terminal 60 is further provided with a wireless communication circuit 612 capable of communication according to a communication protocol such as a wireless LAN that is used in communication between the x-ray sensor 1 and the x-ray control device 5, and a network is configured in which the x-ray sensor 1, the x-ray control device 5, and the mobile terminal 60 communicate with one another. For example, it is assumed that the wireless communication circuit of the x-ray sensor 1, the wireless communication circuit connected to the x-ray control device 5, and the wireless communication circuit 612 of the mobile terminal are mounted to conform to the Wi-Fi Direct standard. Communication between the mobile terminal 60 and the x-ray sensor 1 is established, in which the mobile terminal 60 is a group owner, and a network between the mobile terminal 60 and the x-ray sensor 1 is configured. Next, the mobile terminal 60 invites the x-ray control device 5 for the network, thereby achieving communication between the x-ray sensor 1 and the x-ray control device 5 via the network in which the mobile terminal 60 is the group owner. Here, if, for example, the x-ray sensor 1 and the x-ray control device 5 directly communicate with each other according to an Invitation use case of Wi-Fi Direct, the x-ray sensor 1 and the x-ray control device 5 can perform communication in which synchronization at the time of imaging is more reliable, and thus, radiography can be executed more reliably.

Regarding this point, it is also conceivable, for example, to set the x-ray sensor 1 as a group owner, or to set the communication circuit on the x-ray control device 5 side as a group owner. For example, the x-ray sensor 1 is set as a group owner if the x-ray sensor 1 is touched first by the mobile terminal 60 and then the x-ray control device 5 is touched thereby, and the communication circuit on the x-ray control device 5 side is set as a group owner if the x-ray control device 5 is touched first. Direct communication between the x-ray sensor 1 and the x-ray control device 5 is thereby achieved. Note that "touch" here means to bring one of them close to, or in contact with, the other, or literally means contact in the case of body area network communication, or means to bring them close to each other at a distance at which communication is possible in the case of using a near field wireless communication protocol as mentioned above.

Because the mobile terminal 60 is provided with the wireless communication circuits of both NFC and a wireless LAN, for example, communication can be established using any of these communication methods in the case of establishing communication with the x-ray sensor 1 and the x-ray control device 5 that conform to both NFC and a wireless LAN, and each communication method can be appropriately used depending on the situation at the time of use, resulting in excellent usability. It is useful because, even if the wireless communication circuit of the x-ray sensor 1 conforms to only one of NFC or a wireless LAN, communication can be established according to the available protocol.

Also, the control circuit 66 and the display unit 64 of the mobile terminal 60 can be used as the image processing apparatus 10 and the display device 11, respectively. A captured image can be quickly checked by receiving x-ray image data acquired by the x-ray sensor 1 via a network or NFC and causing the display unit 64 of the mobile terminal 60 to display it. Determination of whether or not an image is a failure is input via the operation unit 65 of the mobile terminal 60, and the display unit 64 shows a display indicating that the image is a failure on the image. If an instruction to perform re-imaging is input via the operation unit 65, imaging is again executed under identical imaging conditions as those for the image that was already captured. An image acquired using the communication circuit 61 is transmitted to a PACS. Alternatively, imaging orders are received from an RIS by the communication circuit 61, and a list of these imaging orders is displayed on the display unit 64. By selecting one of the imaging orders via the operation unit 65, one or a plurality of imaging conditions suitable for this imaging order are displayed. Further, by selecting the imaging order via an operation input by the operation unit 65 or automatically, the communication circuit transmits information on an accumulation time of the x-ray sensor 1 that is associated with the imaging conditions to the x-ray sensor 1, and transmits information on x-ray irradiation conditions such as tube voltage and tube current to the x-ray control device 5. Alternatively, the communication circuit receives irradiation conditions of x-rays that were actually irradiated by the x-ray control device 5. Thus, for example, by using one mobile terminal that is assigned to each of, or a plurality of, members in charge of radiography in a hospital, complete x-ray imaging can be executed, including processing for pairing between the x-ray sensor 1 and the x-ray control device 5, image check processing, receipt of orders from the RIS, data transmission to the PACS, and the like. Part of the aforementioned functions may be omitted, or other functions may be added, depending on, for example, processing performance of the control circuit of the mobile terminal, the size of a display area of the display unit, or other conditions.

For example, a case is possible where a circuit for wireless communication or an interface for performing wireless communication is not implemented in the x-ray control device 5. In this case, only establishment of communication between the x-ray sensor 1 and the mobile terminal is performed, and the functions such as pairing with the x-ray control device 5 and communication with the x-ray control device 5 are not necessary or not used. In this case, for example, a detection circuit for detecting start of x-ray irradiation is provided in the x-ray sensor 1, the x-ray sensor 1 shifts to an accumulating state upon detection of x-ray irradiation from the x-ray tube 4, and thus radiographic image data is obtained.

In addition, communication between the x-ray sensor 1 and the image processing apparatus 10 can also be established using the mobile terminal. If the mobile terminal functions as the image processing apparatus 10 and the display device 11 as mentioned above, communication establishment is performed as described above. In other cases, a communication circuit for near field wireless communication such as NFC is connected also to the image processing apparatus 10, and communication is established by the mobile terminal sequentially touching the image processing apparatus 10.

As above, according to the embodiments of the present invention, wireless connection can be established within the usual x-ray imaging work flow, while special operations therefor by a user are reduced to the minimum.

Other Embodiments

Embodiments of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-131389 filed on Jun. 8, 2012, and No. 2013-074865, filed Mar. 29, 2013, which are hereby incorporated by reference herein in their entirety.

What is claimed is:

1. An X-ray imaging system comprising:
   an X-ray sensor including a wireless slave device and a first identification information communication unit that is associated with said wireless slave device;
   a wireless master device configured to connect wirelessly to said wireless slave device;
   a second identification information communication unit that is associated with said wireless master device and an X-ray tube that irradiates X-rays; and
   an identification information intermediating unit configured to receive and store identification information about said wireless slave device or about said wireless master device in a case in which said identification information intermediating unit is in the vicinity of one of said first and the second identification information communication units, and to transmit the identification information in a case in which said identification information intermediating unit is in the vicinity of the other one of said first and the second identification information communication units,
   wherein the identification information intermediating unit is constituted as a different body from the first identification information communication unit and from the second identification information communication unit, and
   wherein said wireless master device and said wireless slave device establish wireless connection based on the identification information.

2. The X-ray imaging system according to claim 1, wherein said wireless slave device comprises a connection request transmission unit configured to transmit a wireless connection request that includes identification information about said wireless slave device,
   said wireless master device comprises:
      a verification unit configured to verify whether the identification information received from said wireless slave device matches the identification information about said wireless slave device that was acquired through said second identification information communication unit in a state in which said identification information intermediating unit intermediates, and a connection information transmission unit configured to transmit wireless connection information to said wireless slave device if it is confirmed by said verification unit that the identification information received from said wireless slave device is identical to the identification information about said wireless slave device acquired through said second identification information communication unit, and wherein said wireless master device and said wireless slave device establish wireless connection by said wireless slave device setting the wireless connection information received from said wireless master device in said wireless slave device.

3. The X-ray imaging system according to claim 1, wherein said wireless slave device comprises a connection request transmission unit configured to transmit a wireless connection request that includes identification information of the wireless master device acquired through said first identification information communication unit in a state in which said identification information intermediating unit intermediates, said wireless master device comprises:
  a verification unit configured to verify whether identification information of the wireless master device matches the identification information about said wireless master device received from said wireless slave device; and
  a connection information transmission unit configured to transmit wireless connection information to said wireless slave device if it is confirmed by said verification unit that the identification information about said wireless master device is identical to the identification information about said wireless master device received from said wireless slave device, and wherein said wireless master device and said wireless slave device establish wireless connection by said wireless slave device setting the wireless connection information received from said wireless master device in said wireless slave device.

4. The X-ray imaging system according to claim 1, wherein said second identification information communication unit is provided in the vicinity of said X-ray tube.

5. The X-ray imaging system according to claim 1, wherein said identification information intermediating unit is configured to be worn or carried by an operator.

6. The X-ray imaging system according to claim 1, wherein said identification information intermediating unit and said first or the second identification information communication unit are configured to communicate with each other using near field wireless communication.

7. The X-ray imaging system according to claim 1, wherein said identification information intermediating unit and said first or the second identification information communication unit are configured to communicate with each other using contact-type communication, in which a human body is a communication path.

8. The X-ray imaging system according to claim 1, wherein the identification information includes a class code indicating a device class of said wireless slave device or said wireless master device, and a password that is unique to the device in question.

9. The X-ray imaging system according to claim 8, wherein if said identification information intermediating unit receives identification information including the same class code as the class code included in the identification information that is currently stored therein, and also including a password that is different from the password included in the identification information currently stored therein, said identification information intermediating unit updates the identification information.

10. An X-ray imaging system comprising:
an X-ray imaging device including a first identification information communication unit; and
a mobile terminal including:
a first communication unit configured to communicate with said first identification information communication unit and a second identification information communication unit associated with an X-ray generating unit, upon said first identification information communication unit and the second identification information communication unit coming into sufficient proximity with each other;
a second communication unit that is different from said first communication unit and is able to communicate with said first identification information communication unit and the second identification information communication unit by a communication protocol; and
a selecting unit configured to select a set including said X-ray imaging device and the X-ray generating unit in accordance with communication by said first communication unit or said second communication unit.

11. An X-ray imaging system comprising:
an X-ray sensor including a wireless slave device and a first identification information communication unit that is associated with said wireless slave device;
a wireless master device configured to connect wirelessly to said wireless slave device;
a second identification information communication unit that is associated with the said wireless master device and an X-ray tube that irradiates X-rays; and
an identification information intermediating unit configured to receive and store identification information about said wireless slave device or about said wireless master device in a case in which said identification information intermediating unit is in the vicinity of one of said first and the second identification information communication units, and configured to transmit the identification information in a case in which said identification information intermediating unit is in the vicinity of the other one of said first and the second identification information communication units, in a case where said first identification information communication unit and said second identification information communication unit are disposed at positions relative each other such that near field wireless communication therebetween is impossible,
wherein the identification information intermediating unit is constituted as a different body from the first identification information communication unit and from the second identification information communication unit, and
wherein said wireless master device and said wireless slave device establish wireless connection based on the identification information.

12. The X-ray imaging system according to claim 1, wherein said near field wireless communication is communication of at least one of TransferJet, infrared data communication and NFC.

13. The X-ray imaging system according to claim 1, wherein the first identification information communication unit and the second identification information communication unit are respectively disposed at positions where a Near Field Communication is not available.

* * * * *